US012730096B2

(12) United States Patent
Evans et al.

(10) Patent No.: US 12,730,096 B2
(45) Date of Patent: Sep. 8, 2026

(54) METHOD FOR ANALYZING TRACE LEVELS OF SEMI-VOLATILE NITROSAMINES IN SOLID SAMPLES

(71) Applicant: Merck Sharp & Dohme LLC, Rahway, NJ (US)

(72) Inventors: Rebecca Evans, New York, NY (US); Xinxin Han, East Brunswick, NJ (US); Daniel E. Lee, Sayreville, NJ (US); Christine L. Radich, Somerset, NJ (US); Jinjian Zheng, Scotch Plains, NJ (US)

(73) Assignee: Merck Sharp & Dohme, Rahway, NJ (US)

( * ) Notice: Subject to any disclaimer, the term of this patent is extended or adjusted under 35 U.S.C. 154(b) by 376 days.

(21) Appl. No.: 18/577,775

(22) PCT Filed: Jul. 11, 2022

(86) PCT No.: PCT/US2022/036616
§ 371 (c)(1),
(2) Date: Jan. 9, 2024

(87) PCT Pub. No.: WO2023/287670
PCT Pub. Date: Jan. 19, 2023

(65) Prior Publication Data

US 2024/0345038 A1 Oct. 17, 2024

Related U.S. Application Data

(60) Provisional application No. 63/297,463, filed on Jan. 7, 2022, provisional application No. 63/222,502, filed on Jul. 16, 2021.

(51) Int. Cl.
*G01N 30/30* (2006.01)
*G01N 30/14* (2006.01)
(Continued)

(52) U.S. Cl.
CPC ............. *G01N 30/30* (2013.01); *G01N 30/14* (2013.01); *G01N 30/62* (2013.01);
(Continued)

(58) Field of Classification Search
CPC ... G01N 2030/8818; G01N 2030/8827; G01N 2030/8831; G01N 30/30; G01N 30/62;
(Continued)

(56) References Cited

U.S. PATENT DOCUMENTS 4,249,904 A * 2/1981 Rounbehler ......... G01N 31/224 436/178
4,381,408 A * 4/1983 Rounbehler ....... G01N 33/0047 436/107

(Continued)

FOREIGN PATENT DOCUMENTS

CN 106018624 A * 10/2016 ............. G01N 30/02
CN 111323501 A * 6/2020 ............. G01N 30/32

(Continued)

OTHER PUBLICATIONS

Environmental Protection Agency, Method 8070A Nitrosamines by Gas Chromatography, Revision 1, 1996 (Year: 1996).*

(Continued)

*Primary Examiner* — David L Singer
(74) *Attorney, Agent, or Firm* — Sylvia A. Ayler; Catherine Fitch

(57) ABSTRACT

This invention describes a novel method encompassing preparing a nitrosamine sample, adding in relevant chemicals that reduces or eliminates in situ nitrosamine formation, utilizing full evaporation static headspace gas chromatograph coupled with nitrogen phosphorous detector (FE-SHSGC-NPD), and analysis of rapid results in the gaseous phase for sensitive detection of semi-volatile nitrosamines, including NDMA.

17 Claims, 12 Drawing Sheets

(51) Int. Cl.
*G01N 30/62* (2006.01)
*G01N 30/72* (2006.01)
*G01N 33/15* (2006.01)

(52) U.S. Cl.
CPC ......... *G01N 30/7206* (2013.01); *G01N 33/15* (2013.01); *Y10T 436/170769* (2015.01)

(58) Field of Classification Search
CPC ........ G01N 30/72; G01N 30/86; G01N 30/88; G01N 33/15; Y10T 436/170769
USPC .......................................................... 436/107
See application file for complete search history.

(56) References Cited

U.S. PATENT DOCUMENTS

| | | | | |
|---|---|---|---|---|
| 4,501,608 A * | 2/1985 | Cannon | A01N 33/18 | 504/358 |
| 5,324,857 A * | 6/1994 | Shehad | C07C 291/04 | 564/301 |
| 5,441,700 A * | 8/1995 | Markelov | G01N 30/24 | 422/63 |
| 2017/0261482 A1* | 9/2017 | Basheer | G01N 33/1826 | |
| 2021/0285920 A1* | 9/2021 | Xiao | G01N 30/7206 | |

FOREIGN PATENT DOCUMENTS

| | | | |
|---|---|---|---|
| CN | 112083088 A * | 12/2020 | G01N 30/32 |
| WO | 1993022273 A1 | 11/1993 | |

OTHER PUBLICATIONS

Parr et al, NDMA impurity in valsartan and other pharmaceutical products: Analytical methods for the determination of N-nitrosamines, Journal of Pharmaceutical and Biomedical Analysis 164 (2019) 536-549 (Year: 2019).*
Yamada et al, Studies on the Formation of Nitrosamines (VII) The Effects of Some Polyphenols on Nitrosation of Diethylamine, J. Food Hyg. Soc. vol. 19, No. 2, 1977 (Year: 1977).*
Grebel et al, Nitrogen-phosphorus detection and nitrogen chemiluminescence detection of volatile nitrosamines in water matrices: Optimization and performance comparison, Journal of Chromatography A, 1175 (2007) 141-144 (Year: 2007).*
Rundlolf et al, Potential Nitrite Scavengers as Inhibitors of the Formation of N-Nitrosamines in Solution and Tobacco Matrix Systems, J. Agric. Food Chem. 2000, 48, 4381-4388 (Year: 2000).*
Arnold Venema, The Usefulness of the Headspace Analysis-Gas Chromatography Technique for the Investigation of Solid Samples, Journal of High Resolution Chromatography, 13, 537-539, 1990.
Brault, Audrey et al., The full evaporation technique: A promising alternative for residual solvents analysis in solid samples, J. Sep. Sci., 28, 380-386, 2005.
Hu, Jingli et al., Determination of dimethylamine and nitrite in pharmaceuticals by ion chromatography to assess the likelihood of nitrosamine formation, Heliyon, 7:e06179, 1-8, 2021.
Jan Schuberth, Volatile Organic Compounds Determined in Pharmaceutical Products by Full Evaporation Technique and Capillary Gas Chromatography/ Ion-Trap Detection, Anal. Chem., 68, 1317-1320, 1996.
Michael Markelov, Matrix independent headspace gas chromatographic analysis. The full evaporation technique, Analytica Chimica Acta, 276, 235-245, 1993.
Minna Hakkarainen, Developments in multiple headspace extraction, J. Biochem. Biophys. Methods, 70, 229-233, 2007.
Peto, Richard et al., Dose and Time Relationships for Tumor Induction in the Liver and Esophagus of 4080 Inbred Rats by Chronic Ingestion of N-Nitrosodiethylamine or N-Nitrosodimethylamine, Cancer Research, 51, 6452-6469, 1991.
Van Boxtel, Niels et al., Evaluation of the full evaporation technique for quantitative analysisof high boiling compounds with high affinity for apolar matrices, J. Chromatogr. A, 1348, 63-70, 2014.
Wichitnithad, Wisut et al., Development of a Sensitive Headspace Gas Chromatography-Mass Spectrometry Method for the Simultaneous Determination of Nitrosamines in Losartan Active Pharmaceutical Ingredients, ACS Omega, 6, 11048-11058, 2021.
Dutra, Camila B. et al., Determination of volatile N-nitrosamines in sausages by HS-SPME-GC-TEA, Abstracts / Toxicology Letters, 164S, S274-S275, 2006.
Incavo, Joseph A. et al., Simplified method for the determination of N-nitrosamines in rubber vulcanizates, Analytica Chimica Acta, 557, 256-261, 2006.

* cited by examiner

METHOD FOR ANALYZING TRACE LEVELS OF SEMI-VOLATILE NITROSAMINES IN SOLID SAMPLES

CROSS-REFERENCE TO RELATED APPLICATIONS

This application is a national stage application of International Patent Application No. PCT/US2022/036616 filed Jul. 11, 2022, which claims the benefit of U.S. Provisional Patent Application No. 63/222,502, filed Jul. 16, 2021, and U.S. Provisional Patent Application No. 63/297,463, filed Jan. 7, 2022, each of which is incorporated by reference in its entirety herein.

FIELD OF THE INVENTION

The present invention relates to a novel process for analyzing trace level semi-volatile nitrosamines in solid pharmaceutical samples.

BACKGROUND OF THE INVENTION

Most nitrosamines are probable carcinogens with very low acceptable intake limit (AI), e.g. 96 ng/day for N-nitrosodimethylamine (NDMA) R Peto, R Gray, et al., Cancer Res., 51(1991), 6452-69. As a result of nitrosamine levels exceeding AI, many lots of critical drugs have had to be recalled. See for example, <https://www.fda.gov/drugs/drug-safety-and-availability/fda-updates-and-press-announcements-ndma-metformin> and <https://www.fda.gov/drugs/drug-safety-and-availability/fda-updates-and-press-announcements-angiotensin-ii-receptor-blocker-arb-recalls-valsartan-losartan><https://www.fda.gov/news-events/press-announcements/fda-requests-removal-all-ranitidine-products-zantac-market>.

There are two major challenges in nitrosamine testing: the vast number of products that need to be tested and the high sensitivity of methods needed to meet regulatory expectations. There are approximately 1.13 billion people with hypertension, over 463 million people with diabetes worldwide, and heartburn occurs in roughly 1.5 billion people on a weekly basis. There are hundreds of thousands batches of these drug products on the market that need to be tested for nitrosamines. In addition, pharmaceutical companies need to perform confirmatory testing across multiple lots if a potential risk is identified in the drug products, which could affect a large portion of the drug products on the market or in development. Furthermore, this is a rapidly evolving regulatory environment with major regulatory agencies issuing guidance on the control of nitrosamines in human drugs. According to recent EMA guidance, drug manufacturers are required to demonstrate that the nitrosamine level is consistently below 10% of AI to justify omission of a specification [(e.g. 4.8 ppb NDMA in metformin HCl based on a maximum daily dose of 2 g); EMEA/H/A-5(3)/1490. Procedure under Article 5(3) of Regulation EC (No) 726/2004, 25 Jun. 2020, Nitrosamine impurities in human medicinal products]. This is especially difficult for formulated drug products with complex matrices, including popular drugs like sartans, ranitidine, nizatidine and metformin.

Typically, nitrosamines are separated from sample matrix using liquid chromatography (coupled with high resolution mass spectrometer (HRMS) is often used to achieve the desired sensitivity and selectivity. However, LC-HRMS is not suitable for routine use due to high instrument cost, high maintenance cost and extensive analyst training. GC coupled with mass spectrometer (MS), thermal energy analyzer (TEA), or nitrogen phosphorous detector (NPD) has been used to analyze nitrosamines at trace levels. However, the challenge with these methods often lies in how to effectively extract nitrosamines from the sample matrix for GC analysis, and how to prevent in situ formation of nitrosamines.

Although MS coupled with liquid chromatography (LC) or gas chromatography (GC) is capable of detecting nitrosamines at low ppb level, it is difficult to achieve the same sensitivity consistently and the throughput is often limited due to high instrument operating cost, frequent instrument maintenance, extensive sample preparation and relatively complex data processing. Additionally, methodologies such as GC with TEA or NPD are often limited by sensitivity. Nevertheless, methods based on MS detection still dominate the nitrosamine testing despite the high cost and extensive maintenance.

There are two techniques to introduce samples for GC analysis, direct injection and headspace sampling. Direct injection often requires extensive sample preparation to minimize the matrix interference, often resulting in product-specific methods. The sensitivity is limited by the solubility of sample in a given diluent and the efficiency to extract nitrosamines of interest into a suitable solvent. It is not uncommon that the solvent with the highest solubility may not be suitable for GC analysis. For drug products with complex sample matrices, it is difficult to achieve the desired sensitivity for nitrosamines for GC with direct injection.

Headspace sampling is a technique that extracts volatile analytes to headspace prior to GC analysis, which minimizes matrix effects of non-volatile compounds. See for example, Kolb, B., Ettre, L. S., Static Headspace—Gas Chromatography: Theory and Practice, Second edition, Wiley-Interscience, 2006 The most common type of headspace sampling is static headspace sampling (SHS), in which the sample is dissolved in a solvent in a headspace vial, and an equilibrium is established between headspace and solution upon heating the vial, and a portion of the headspace is analyzed. This technique is very sensitive for volatile analytes, which can be easily driven to headspace. However, the sensitivity suffers for analytes with high boiling points such as nitrosamines, which mainly partition in the liquid phase. Several other headspace sampling techniques have been used to improve sensitivity including: 1) dynamic headspace sampling (DHS): 2) multiple headspace extraction (MHE): and 3) full evaporation technique (FET). See Venema, A., J. High Resolution Chroma., Vol 13, 1990, 537-539; Hakkarainen, M., J. Biochem. Biophys. Methods 70 (2007) 229-233; Markelov, M. Analytica Chimica Acta, 276 (1993) 235-245; Schubert, J., Anal. Chem. 1996, 68, 1317-1320; Brault, A. et. al., J. Sep. Sci. 2005, 28, 380-386; Boxtel, N.; Wolfs, K.; Schepdael, A.; Adams, E., J. Chromatogr. A, 1348 (2014) 63-70.

DHS utilizes an inert gas to continuously remove the analytes from the headspace, by trapping them using either cryogenic or sorbent traps, and thermally desorbing the trapped analytes before injecting into GC for analysis. DHS is an exhaustive extraction technique and often takes time to completely extract the analytes from the sample matrix as the extraction process proceeds exponentially. Compared to SHS-GC, it is often more difficult to automate DHS-GC analysis, which in turn limits the throughput.

MHE, in principle, is DHS carried out in stepwise fashion. One difference is that the total amount of analyte in a solid sample can be calculated theorectically after only a few successive extractions, typically 3 to 5 extractions, thus reducing the extraction time. However, with MHE each extraction has to be analyzed separately, resulting in lower sensitivity compared to DHS especially for analytes with high partition coefficient such as nitrosamines.

FET is based on a single-step, near-complete transfer of analytes from a condensed matrix, either liquid or solid, into a confined vapor phase. The full evaporation applies only to analytes, and not necessarily the sample matrix, and thus can be applied to both volatile and non-volatile matrices. In FET, a small amount of liquid sample is enclosed in a headspace vial. Upon heating, almost all volatile components are separated from the non-volatile components and transferred to headspace. This helps to minimize the effect of complex sample matrix and facilitate quantitation. For highly volatile analytes, FET does not have an advantage in terms of sensitivity, which has been reported to fall between direct injection and static headspace sampling for volatile analytes. However, for semi-volatile nitrosamines, FET could be used to improve the sensitivity.

There remains a need for a simple, universal method for sensitive, accurate, and specific detection of semi-volatile nitrosamines, including NDMA, which inhibits the in situ formation of nitrosamines

SUMMARY OF THE INVENTION

The present invention relates to a method utilizing full evaporation static headspace gas chromatography method coupled with GC detection for high throughput analysis of semi-volatile nitrosamines including NDMA (N-nitrosodimethylamine), N-Nitrosodiethylamine (NDEA), N-nitrosoethylisopropylamine (NEIPA), N-nitrosodiisopropylamine (NDIPA), N-nitrosodibutylamine (NDBA), N-nitrosomethylphenylamine (NMPA) and N-nitrosomorpholine (NMORP) NDMA (N-nitrosodimethylamine), NDEA (N-nitrosodiethylamine), NIPEA (N-nitrosoethylisopropylamine), NDIPA (N-nitrosodiisopropylamine), NDBA (N-nitrosodibutylamine), NMBA (N-nitroso-N-methyl-4-aminobutyric acid), NMPA (N-nitrosomethylphenylamine), and NMORP (nitrosomorpholine). The method offers accurate quantitation, superior sensitivity (e.g., quantitation limit approximately 0.25 part per billion (ppb) for NDMA), simple sample preparation, low cost and quick implementation. In situ formation of NDMA, a common issue for headspace sampling, is completely inhibited by this method.

The present invention further relates to improved methods for analyzing trace level semi-volatile nitrosamines in solid samples. This method can be coupled with most GC detectors, including mass spectrometer (MS), nitrogen-phosphorus detector (NPD), thermal energy analyzer (TEA), nitrogen chemiluminescence detector (NCD) or flame ionization detector (FID). An aspect of this invention is realized when the GC detector is NPD. The invention further relates to methods for analyzing trace level semi-volatile nitrosamines in solid samples without sample extraction to eliminate solubility or solvent incompatibility issues, and can be used as a universal method for different products "as is" or with minor modifications. Thus, another aspect of the invention is realized by a method for analyzing trace level semi-volatile nitrosamines in solid samples to eliminate solubility or solvent incompatibility issues.

The invention further relates to a method for analyzing nitrosamine impurities in a pharmaceutical sample that reduces or eliminates in situ nitrosamine formation. An embodiment of this aspect of the invention comprises:

a) heating a pharmaceutical sample containing one or more nitrosamine in the presence of one or more nitrosating inhibitors, and b) analyzing the nitrosamines in the headspace.

An embodiment of this invention is realized when the nitrosamine(s) from the pharmaceutical sample into headspace is displaced without in situ formation of additional nitrosamine(s).

An embodiment of this invention is realized when the method is conducted using a headspace vial.

Another embodiment of this aspect of the invention is realized when the nitrosamine impurity being analyzed is semi-volatile.

Another embodiment of this aspect of the invention is realized when the nitrosating Inhibitor/nitrite scavenger is selected from pyrogallol, phloroglucinol, pyrrole, 2,5-dimethylpyrrole, catechol, ascorbic acid, hydrazine, propylgallate, gallic acid and/or competing reactive amines diphenylamine, and N-methyl aniline. A subembodiment of this aspect of the invention is realized when the nitrosating inhibitor is pyrogallol. Another subembodiment of this aspect of the invention is realized when the nitrosating inhibitor is pyrrole or 2,5-dimethylpyrrole. Another subembodiment of this aspect of the invention is realized when the nitrosating inhibitor is phloroglucinol. Another subembodiment of this aspect of the invention is realized when the nitrosating inhibitor is catechol. Another subembodiment of this aspect of the invention is realized when the nitrosating inhibitor is ascorbic acid. Another subembodiment of this aspect of the invention is realized when the nitrosating inhibitor is caffeic acid. Another subembodiment of this aspect of the invention is realized when the nitrosating inhibitor is hydrazine. Another subembodiment of this aspect of the invention is realized when the nitrosating inhibitor is propylgallate. Another subembodiment of this aspect of the invention is realized when the nitrosating inhibitor is gallic acid. Another subembodiment of this aspect of the invention is realized when the nitrosating inhibitor is diphenylamine. Another subembodiment of this aspect of the invention is realized when the nitrosating inhibitor is N-methyl aniline. Yet another subembodiment of this aspect of the invention is realized when the nitrosating inhibitor is pyrogallol, phloroglucinol, pyrrole, 2,5-dimethylpyrrole, catechol, ascorbic acid, hydrazine, propylgallate, or gallic acid combined with competing reactive amine diphenylamine or N-methyl aniline. Still another subembodiment of this aspect of the invention is realized when the nitrosating inhibitor is pyragallol in combination with diphenylamine or methyl aniline. Another subembodiment of this aspect of the invention is realized when the nitrosating inhibitor is pyragallol in combination with diphenylamine. Another subembodiment of this aspect of the invention is realized when the nitrosating inhibitor is phloroglucinol in combination with diphenylamine or methyl aniline. Another subembodiment of this aspect of the invention is realized when the nitrosating inhibitor is phloroglucinol in combination with diphenylamine.

An embodiment of this invention is realized when the nitrosating inhibitor is in a diluent comprising an acid and solvent. An aspect of this embodiment of the invention is realized when the concentration of nitrosating inhibitor in the diluent is at least 1 mg/mL. A subembodiment of this aspect of the invention is realized when the concentration of nitrosating inhibitor in the diluent is from 1 mg/mL to 200 mg/mL, preferably about 20 mg/mL.

Still another subembodiment of this aspect of the invention is realized when the nitrosating inhibitor is pyrogallol, phloroglucinol, pyrrole. 2,5-dimethylpyrrole, catechol, ascorbic acid, caffeic acid, hydrazine, propylgallate, and/or gallic acid in a diluent at a concentration of at least 1 mg/mL. Another subembodiment of this aspect of the invention is realized when the concentration of pyrogallol, phloroglucinol, pyrrole, 2,5-dimethylpyrrole, catechol, ascorbic acid, caffeic acid, hydrazine, propylgallate, and/or gallic acid in the diluent is from 1 mg/mL to 200 mg/mL. Another subembodiment of this aspect of the invention is realized when the concentration of pyrogallol, phloroglucinol, pyrrole, 2,5-dimethylpyrrole, catechol, ascorbic acid, caffeic acid, hydrazine, propylgallate, and/or gallic acid in the diluent is from 10 mg/mL to 50 mg/mL. Another subembodiment of this aspect of the invention is realized when the nitrosating inhibitor is pyrogallol at a concentration of about 20 mg/mL.

An embodiment of this invention is realized when the temperature of the pharmaceutical sample is heated to about 60° C. to about 200° C., preferably 90° C. to 130° C., more preferably 95° C. to 115° C.

Another embodiment is realized when the acid is non-volatile and selected from the group consisting of phosphoric acid, sulfuric acid, methanesulfonic acid and the like. A subembodiment of this invention is realized when the acid is phosphoric acid. Another subembodiment of this aspect of the invention is realized when the nitrosating inhibitors is dissolved in a solvent with a medium boiling point (i.e. 60-100° C.) wherein the organic solvent or solvent mixture is selected from water, methanol, acetonitrile, acetone, ethanol, isopropanol, and 1-propanol. Another subembodiment of this aspect of the invention is realized when the solvent is isopropanol.

A subembodiment of this aspect of the invention is realized when the semi-volatile nitrosamine has a boiling point below: 250° C. An aspect of this embodiment of the invention is realized when the semi-volatile nitrosamine is NDMA.

Another embodiment of the invention is realized when the amount of diluent is small enough for the solvent therein to fully evaporate during extraction at a vapor pressure below 75 psi but large enough to reduce or completely inhibit in situ formation of nitrosamines. A subembodiment of this aspect of the invention is realized when the ratio of diluent to the nitrosamine containing pharmaceutical sample is from 1:5 to 50:1, preferably about 2:1 (e.g. 50 mg diluent to 25 mg sample).

Another embodiment of this invention is realized when the nitrosamine containing pharmaceutical sample is a solid. Another embodiment of this invention is realized when the nitrosamine containing pharmaceutical sample is a liquid.

An embodiment of this invention is realized when the nitrosamines in the gaseous headspace phase are separated by gas chromatography (GC).

Another embodiment of this invention is realized when the nitrosamines in the gaseous headspace phase are analyzed using a GC detector selected from the group consisting of mass spectrometer (MS), nitrogen-phosphorus detector (NPD), thermal energy analyzer (TEA), nitrogen chemiluminescence detector (NCD) or flame ionization detector (FID). An aspect of this embodiment of the invention is realized when the GC detector is NPD. Still another embodiment of the invention is realized when GC is coupled with detectors such as MS, NCD, TEA or NPD to provide high sensitivity and selectivity for nitrosamine analysis. Another subembodiment of this aspect of the invention is realized when full evaporation static headspace GC with NPD (FE-SHSGC-NPD) is employed.

Further aspects of this invention is realized upon review of the specification as a whole.

BRIEF DESCRIPTION OF THE DRAWINGS

The present invention and various aspects, features and advantages thereof are explained in detail below with reference to exemplary and therefore non-limiting embodiments, and with the aid of the drawings, which constitute a part of this specification and include depictions of the exemplary embodiments. In these drawings.

DETAILED DESCRIPTION OF THE INVENTION

Process Instrument Conditions

Figure 1:
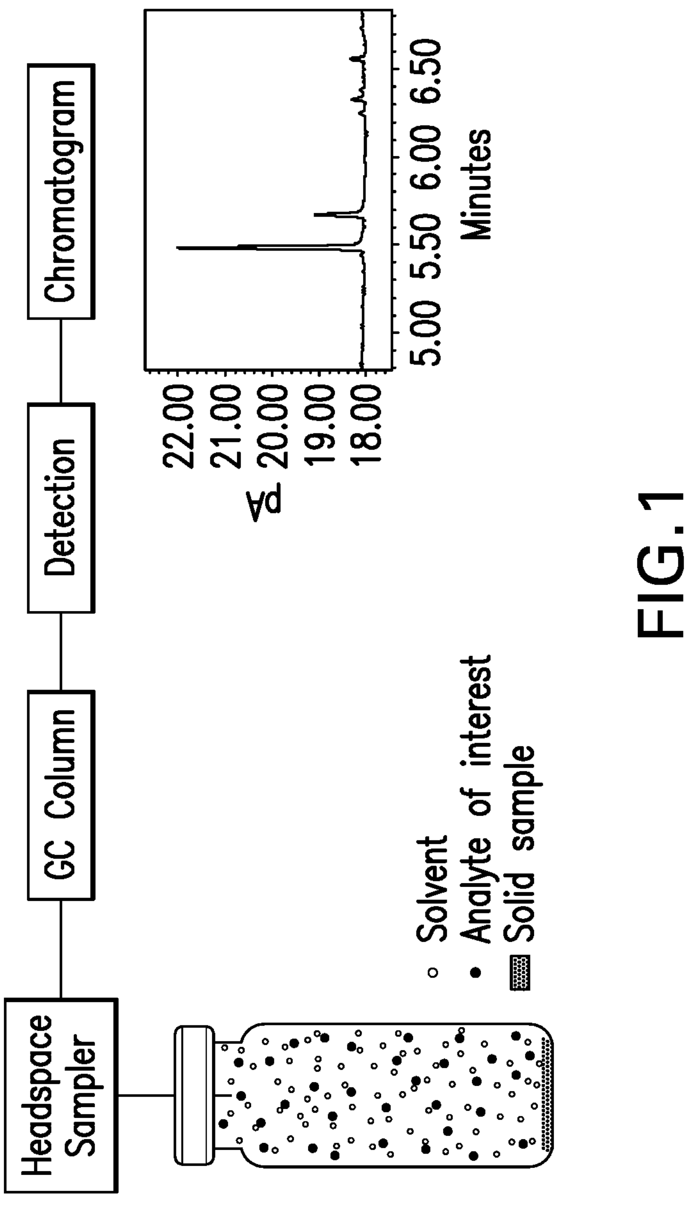
FIG. 1 shows a schematic illustration of FE-SHSGS-NPD method.

Traditional analytical techniques such as LC-UV or GC-FID do not provide the required sensitivity and/or specificity for analyzing nitrosamine analytes. Most methods utilize mass spectrometry detection (MS) detection to achieve the required sensitivity and selectivity. Although MS coupled with liquid chromatography (LC) or gas chromatography (GC) is capable of detecting nitrosamines at low ppb level, it is difficult to achieve the same sensitivity consistently and the throughput is often limited due to high instrument operating cost, frequent instrument maintenance and relatively complex data processing. Several other methodologies have been reported including thermal energy analyzer (TEA), nitrogen chemiluminescence detection (NCD), and nitrogen phosphorous detection (NPD). However, TEA or NCD is often limited by its sensitivity, while NPD is not as specific as TEA or NCD. Methods based on MS detection still dominates the nitrosamine testing despite the high cost and extensive maintenance.

This invention describes a method for analyzing nitrosamines in pharmaceutical samples using full evaporation headspace gas chromatography with a GC detector. An aspect of this invention is realized when the method used is full evaporation headspace gas chromatography with NPD as a GC detector. The method offers superior sensitivity and is suitable for the analysis of common nitrosamines, such as NDMA, NDEA, NEIPA, NDIPA, NDBA, NMPA, and NMORP in drug substances and drug products. Thus, an embodiment of this invention is a method for analyzing nitrosamines in pharmaceutical samples using full evaporation static headspace gas chromatograph with nitrogen-phosphorous detection (FE-SHSGC-NPD). A subembodiment of this aspect of the invention is realized when the method is used to analyze semi-volatile nitrosamine containing pharmaceutical samples as exemplified in FIG. 5.

Although this invention exemplifies a method for analyzing nitrosamines using nitrogen phosphorous detector (NPD) this method can be coupled with any GC detector including MS, TEA, NCD or FID to achieve the desired sensitivity and selectivity. Thus, an aspect of this invention includes GC detectors MS, TEA, NCD, NPD, or FID. The technique is simple, sensitive and fast, and can be easily implemented in a supply analytical laboratory. The simple sample preparation enables this method to be used for nitrosamines in different drug substances or drug products as is or with minor modifications.

Example Instrument Parameters

The instrument used for the analysis was Agilent 7890B GC system equipped with nitrogen-phosphorous detector, and Agilent 7697A headspace sampler.

Example GC parameters are shown below:

| | |
|---|---|
| GC column: | BD-Wax, 30 m × 0.25 mm, 0.5 μm film thickness or equivalent |
| Inlet Temperature: | 200° C. |
| Split Ratio: | 5:1 |
| Carrier Gas: | Helium |
| Flow Rate: | Constant flow at flow rate 3 mL/min |
| Detector: | Nitrogen Phosphorous Detector (NPD). Temperature: 330° C. Fuel flow (Hydrogen): 3 mL/min Oxidizer flow (Air): 60 mL/min Makeup gas: Nitrogen, constant makeup at 5 mL/min Recommended Offset: 20 pA |
| Oven Temperature Program: | Hold 60° C. for 1.5 min, ramp at 20° C./min to 150° C., then 40° C./min to 240° C. and hold for 3 min |
| Total run time: | 11.25 min |

Example Headspace parameters are shown below:

| | |
|---|---|
| Vial size: | 10 mL |
| Vial oven temperature: | 115° C. |
| Injection volume (Sample Loop): | 1 mL |
| Loop temperature: | 160° C. |
| Transfer line temperature: | 170° C. |
| Vial shaking: | high |
| GC cycle time: | 14 min |
| Vial equilibration time: | 15 min |
| Pressure equilibration time: | 0.1 min |
| Injection time: | 0.5 min |
| Vial fill mode: | Fill to pressure at 30 psi |

-continued

Example 1

Shown in FIG. 1 is a schematic illustration of this invention. A solid sample (e.g. tablet) is ground into fine powder. A portion of the powder (e.g. 20-100 mg) is weighed into a headspace vial. A small volume of volatile solvent containing nitrosation inhibitor (e.g. 50 μL 20 mg/mL pyrogallo+0.1% phosphoric acid in IPA) is added. The headspace vial is sealed, and is subjected to headspace extraction at high temperature for extended period (e.g. 115° C. for 15 min). An aliquot of the headspace is injected into a GC column (e.g. DB-Wax) to separate nitrosamine from other volatile components, followed by a sensitive detection using NPD. The nitrosamine in the solid sample is quantitated using an external standard. As shown in FIG. 1, high sensitivity (e.g. below 1 ppb NDMA) can be achieved as the solvent is fully evaporated and there is no headspace-liquid phase partition. Thus, an aspect of this invention is realized by a method for analyzing nitrosamine analytes in pharmaceutical samples that reduces or eliminates in situ nitrosamine formation with a sensitivity level below 1 part per billion nitrosamines. The in situ formation of nitrosamine is minimized with the addition of a nitrosating inhibitor.

Example 2

Figure 2B:
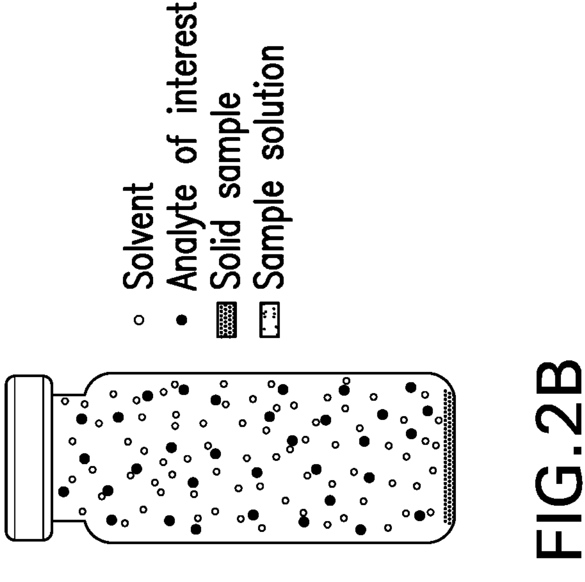
FIG. 2B shows a full evaporation static headspace sampling (FE-SHS).
Figure 2A:
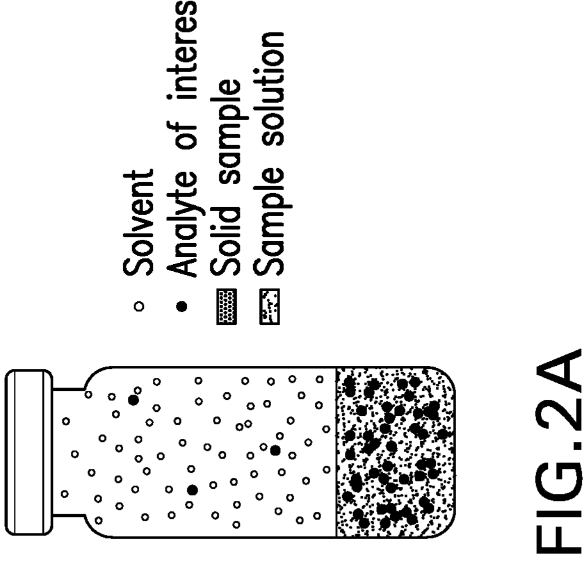
FIG. 2A shows a schematic comparison of traditional static headspace sampling (SHS).

FIG. 2 shows a schematic comparison of traditional static headspace sampling (SHS: Sample A) and full evaporation static headspace sampling (FE-SHS: Sample B). In traditional SHS, the analyte of interest (e.g. nitrosamine) mainly stays in the liquid phase due to its high partition coefficient, resulting in low sensitivity. In FE-SHS, analyte of interest and the solvent is fully evaporated into headspace while the sample matrix is not volatized. Without the undesirable partition, better sensitivity can be achieved even though a smaller amount of sample is used.

Example 3

Figure 3:
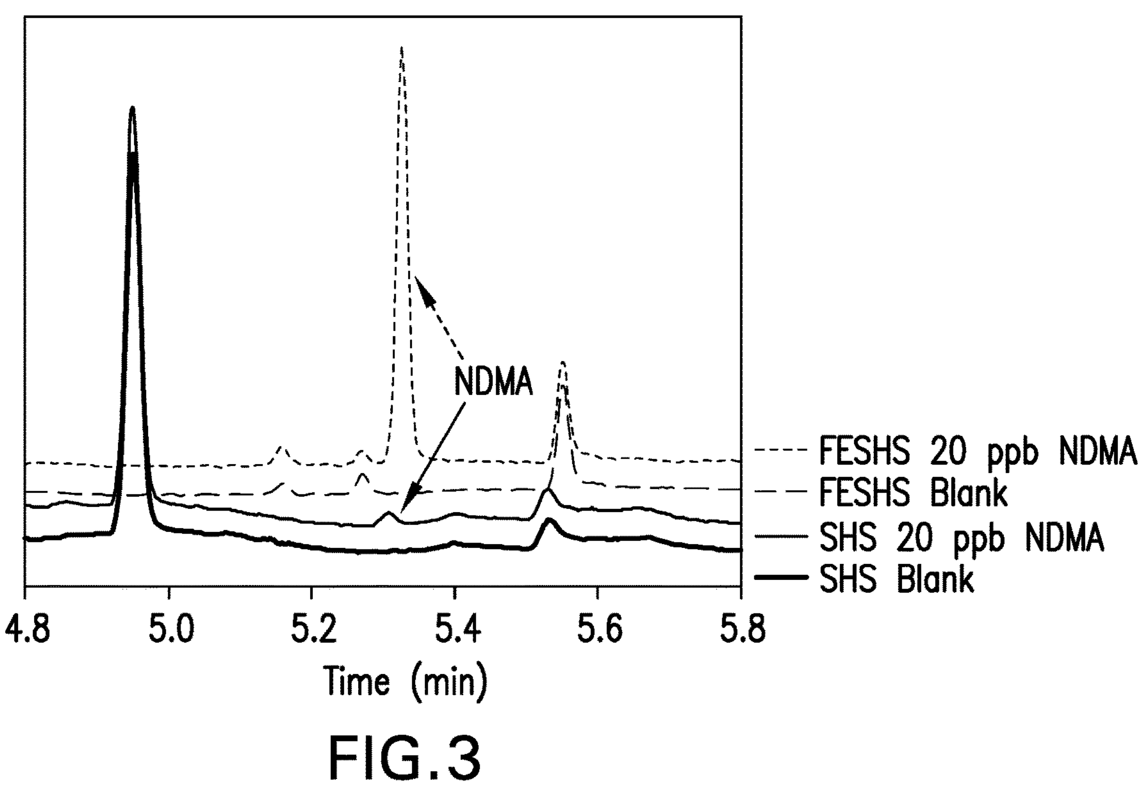
FIG. 3. Comparison of method sensitivity using static headspace sampling and full evaporation static headspace sampling.

The experimental results shown in FIG. 3 illustrates the sensitivity achieved with static headspace sampling and full evaporation static headspace sampling. For static headspace sampling, 1 mL of 2 ng/mL NDMA in DMSO was added to a 10 mL headspace vial, which corresponds to 20 ppb NDMA with respect to 1 mL of 100 mg/ml sample. The vial is heated at 115° C. for 15 min. The injection volume is 1 mL and the split ratio is 5:1. For FE-SHS, 50 μL of 20 ng/mL NDMA in diluent containing 20 mg/mL pyrogallol and 0.1% phosphoric acid in IPA was added to a 10 mL headspace vial, which corresponds to 20 ppb with respect to 50 mg sample. The vial is heated at 115° C. for 15 min, and 1 mL headspace is injected with a split ratio of 5:1. The sensitivity with FE-SHS is 38 times higher than that with SHS. The improved sensitivity in FE-SHS can be attributed to the elimination of headspace-liquid partition. For the data shown in FIG. 3, DMSO was used as diluent as it provided high solubility for drug substances such as valsartan or metformin HCl, and had a high boiling point, a preferred property for SHS. However, the injection volume for SHS is limited due to "phase soaking" effect of condensed DMSO solvent. There is no such limitation for FE-HSGC as IPA had a low boiling point and did not affect the chromatographic behavior of NDMA. As a result, the injection volume can be easily increased for FE-SHS (e.g. from 1 mL to 5 mL) to further improve the sensitivity.

Example 4: Method Sensitivity and Linearity

Figure 4:
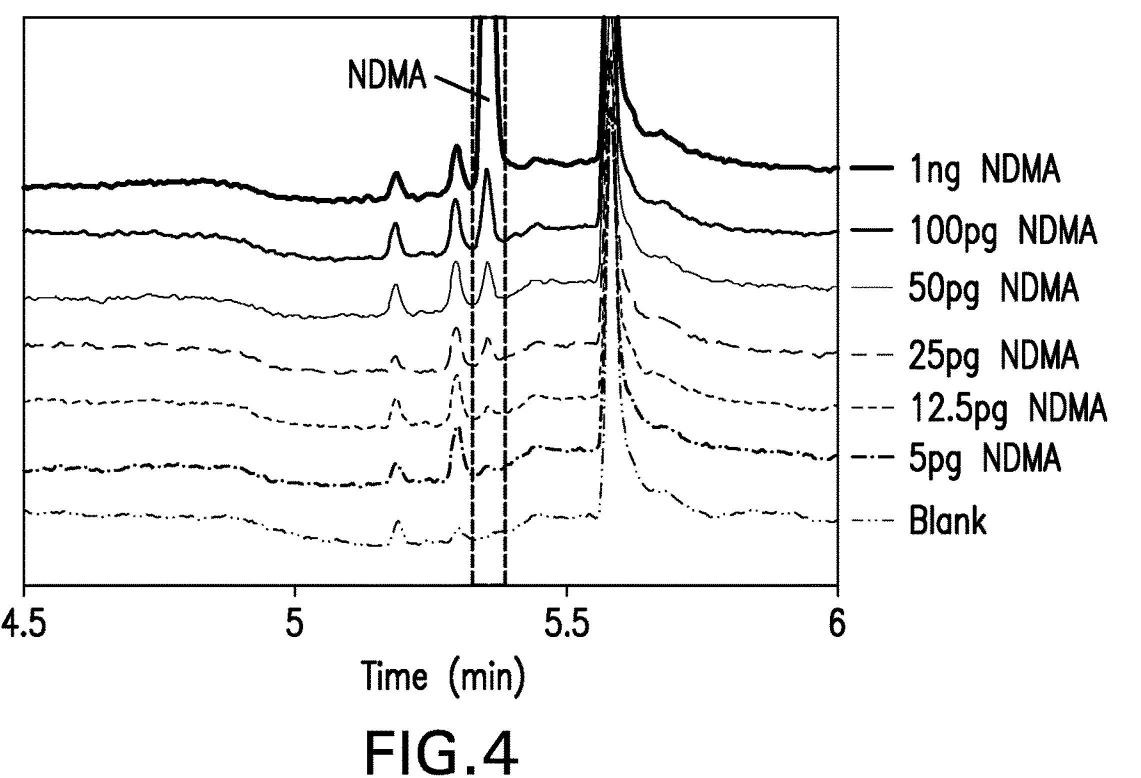
FIG. 4 An analysis of method sensitivity and linearity shown by overlaid chromatograms of blank and NDMA standard solutions obtained using FE-HSGC-NPD.

FIG. 4 shows the overlaid chromatograms of blank and NDMA standard solutions obtained using FE-HSGC-NPD. A DB-Wax column (30 m×0.25 mm, 0.5 μm film thickness) was used. The carrier gas was helium at constant flow rate at 3 mL/min. The oven temperature was held at 60° C. for 1.5 min, then ramped up at 20° C./min to 150° C. then 40° C./min to 240° C., and held at 240° C. for 3 min. The diluent contained 20 mg/mL pyrogallol and 0.1% phosphoric acid in IPA. For each solution, 50 μl was pipetted to a 10-mL headspace vial, capped and crimped tightly. The vial was heated at 115° C. for 15 min, and 1-mL headspace was injected with a split ratio of 5:1. The NDMA concentrations range from 0.1 to 20 ng/ml, corresponding to 0.1 ppb to 20 ppb relative to 50 mg metformin HCl drug substance. The quantitation limit was estimated to be 0.25 ppb based on a signal to noise ratio of 10:1, and the detection limit was estimated to be 0.10 ppb based on a signal to noise ratio of 3:1. The sensitivity obtained using this method meets the regulatory requirement, e.g. 4.8 ppb NDMA in metformin HCl based on a maximum daily dose of 2 g.

Figure 5:
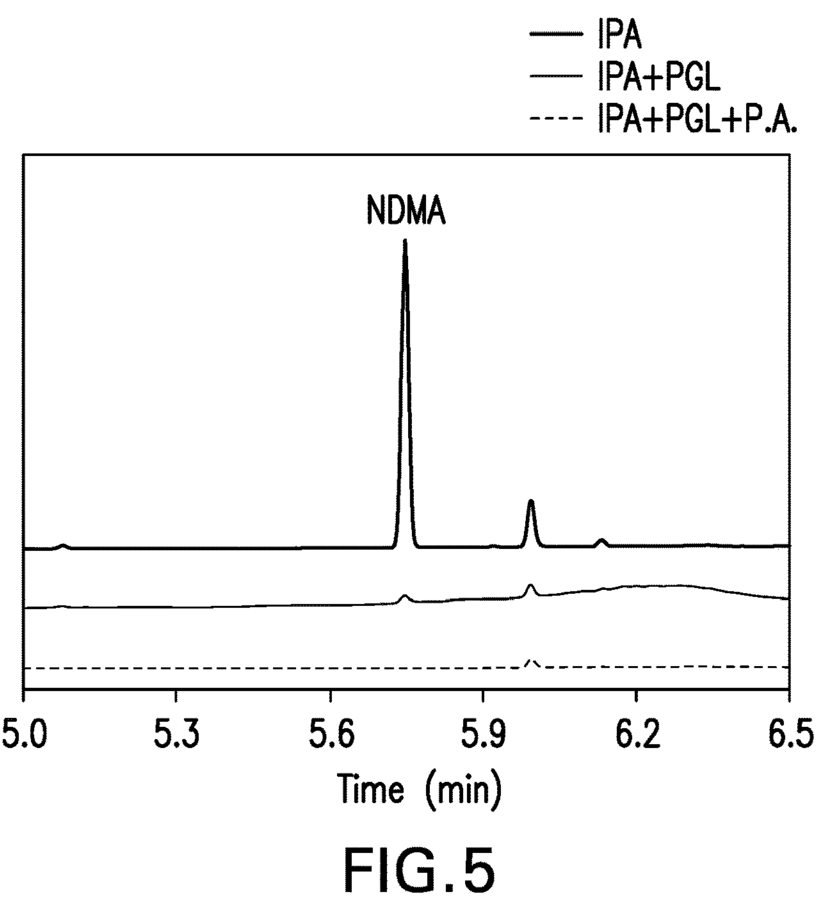
FIG. 5 shows the inhibition of in situ formation of NDMA in metformin HCl drug substance with and without pyrogallol (PGL) during FE-SHSGC-NPD analysis.

Example 5: Inhibition of In Situ Formation of NDMA in Metformin HCl by FE-HSGC-NPD FIG. 5 shows the inhibition of in situ formation of NDMA in metformin HCl drug substance during FE-HSGC-NPD analysis. A DB-Wax column (30 m×0.25 mm, 0.5 μm film thickness) was used. The carrier gas was helium at constant flow rate at 3 mL/min. The oven temperature was held at 50° C. for 1.5 min, then ramped up at 20° C./min to 150° C. then 40° C./min to 240° C., and held at 240° C. for 1 min. About 30 mg metformin HCl drug substance was added to a 10-mL headspace vial, along with 50 μl diluent containing 20 mg/mL pyrogallol and 0.1% phosphoric acid in IPA. The vial was heated at 115° C. for 15 min, and 1-mL headspace was injected with a split ratio of 5:1. Several nitrosation inhibitors have been evaluated including pyrrole, 2,5-dimethylpyrrole, pyrogallol, phloroglucinol, catechol, ascorbic acid, hydrazine, propylgallate and gallic acid. Exemplified in FIG. 5 is the combination of pyrogallol and phosphoric acid in isopropanol solvent, which provided the best inhibition effect. When IPA diluent is used, about 1000 ppb was detected in a metformin HCl material in which no NDMA was detected using a validated LC/MS method (<10 ppb). The NDMA level decreased to 28 ppb with the addition of 20 mg/mL pyrogallol in IPA, and to 0.7 ppb with the addition of both 20 mg pyrogallol and 0.1% phosphoric acid in IPA. Therefore, the risk of false positive due to in situ NDMA formation is deemed negligible (i.e., at least 99.93% of the in situ nitrosation reaction was inhibited) It was unexpected that pyrogallol inhibited the nitrosation more effectively in the presence of phosphoric acid as nitrosation is believed to be catalyzed by acid. One explanation is that under acidic conditions (pH is ~2.5 for 0.1% phosphoric acid), dimethylamine exists as protonated base, resulting in slow nitrosation while pyrogallol is more effective as a nitrosation inhibitor. One additional benefit of phosphoric acid is that the amine impurities in the sample matrix are protonated and become non-volatile, and do not contribute to the interference in GC separation.

Example 6: Analysis of Common Nitrosamines

Figure 6:
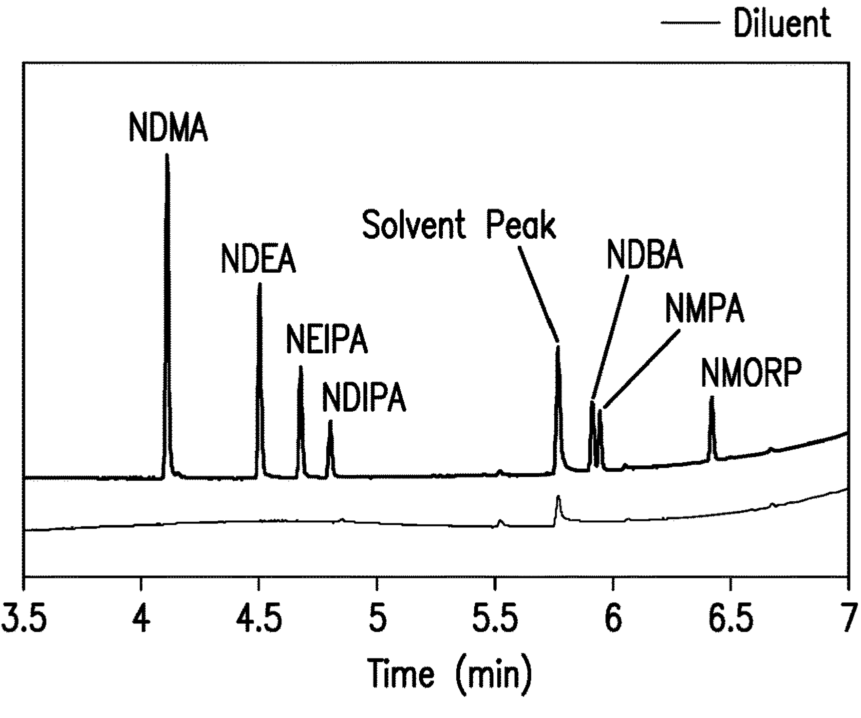
FIG. 6. Analysis of common nitrosamines including NDMA, NDEA, NEIPA, NDIPA, NDBA, NMPA, and NMORP using FE-HSGC-NPD.

FIG. 6 shows analysis of common nitrosamines including NDMA, NDEA, NEIPA, NDIPA, NDBA, NMPA, and NMORP using FE-HSGC-NPD and further demonstrates the unversality of this method. A DB-Wax column (30 m×0.25 mm, 0.5 μm film thickness) was used. The carrier gas was helium at constant flow rate at 2 mL/min. The oven temperature was held at 70° C. for 1 min, then increased at 25° C./min to 240° C., and held at 240° C. for 1 min. The diluent contained 20 mg/mL pyrogallol and 0.1% phosphoric acid in IPA. The standard solution contained 500 ng/ml each of NDMA, NDEA, NEIPA, NDIPA, NDBA, NMPA, and NMORP, and 40 μl was added to a 20-mL headspace vial, capped and crimped tightly. The vial was heated at 150° C. for 30 min, and 1-mL headspace is injected with a split ratio of 20:1.

Example 7: Analysis of NDMA in Metformin-Sitagliptin Instant Release Tablets

Figure 7:
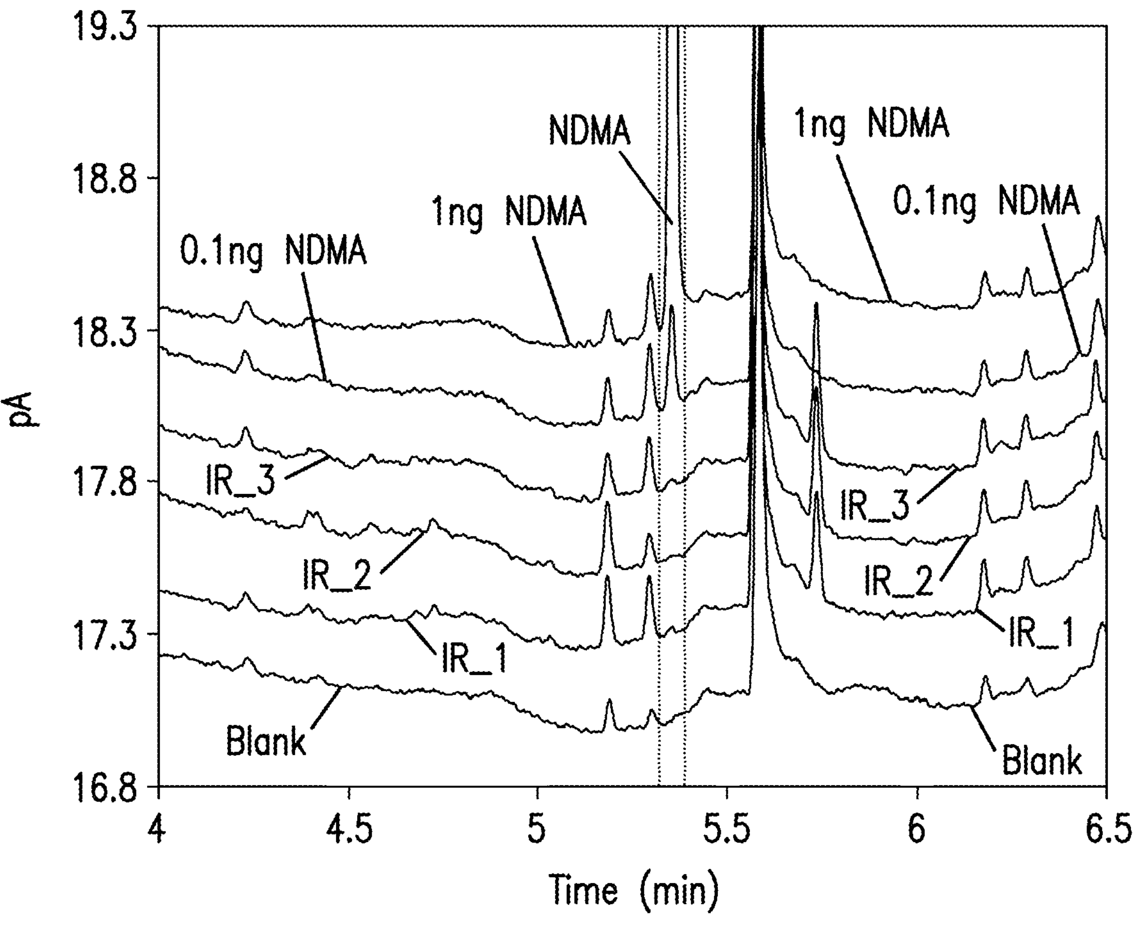
FIG. 7: Analysis of NDMA in metformin-sitagliptin instant release tablets

FIG. 7 shows the analysis of NDMA in metformin-sitagliptin instant release tablets. A DB-Wax column (30 m×0.25 mm, 0.5 μm film thickness) was used. The carrier gas was helium at a constant flow rate of 3 mL/min. The oven temperature esd held at 60° C. for 1.5 min, then increased by 20° C./min to 150° C., followed by 40° C./min to 240° C., and finally held at 240° C. for 3 min. Ground tablet powder equivalent to ~21 mg metformin HCl drug substance was added to a 10 mL headspace vial, along with 50 μL diluent containing 20 mg/mL pyrogallol and 0.1% phosphoric acid in IPA. The vial was heated at 115° C. for 15 min, and 1 mL headspace was injected with a split ratio of 5:1. The quantitation limit for NDMA is 4.8 ppb, corresponding to 10% of the acceptable intake limit of 96 ng/day and maximum daily dose of 2 g.

Example 8: Analysis of NDMA in Metformin-Sitagliptin Extended Release Tablets

Figure 8:
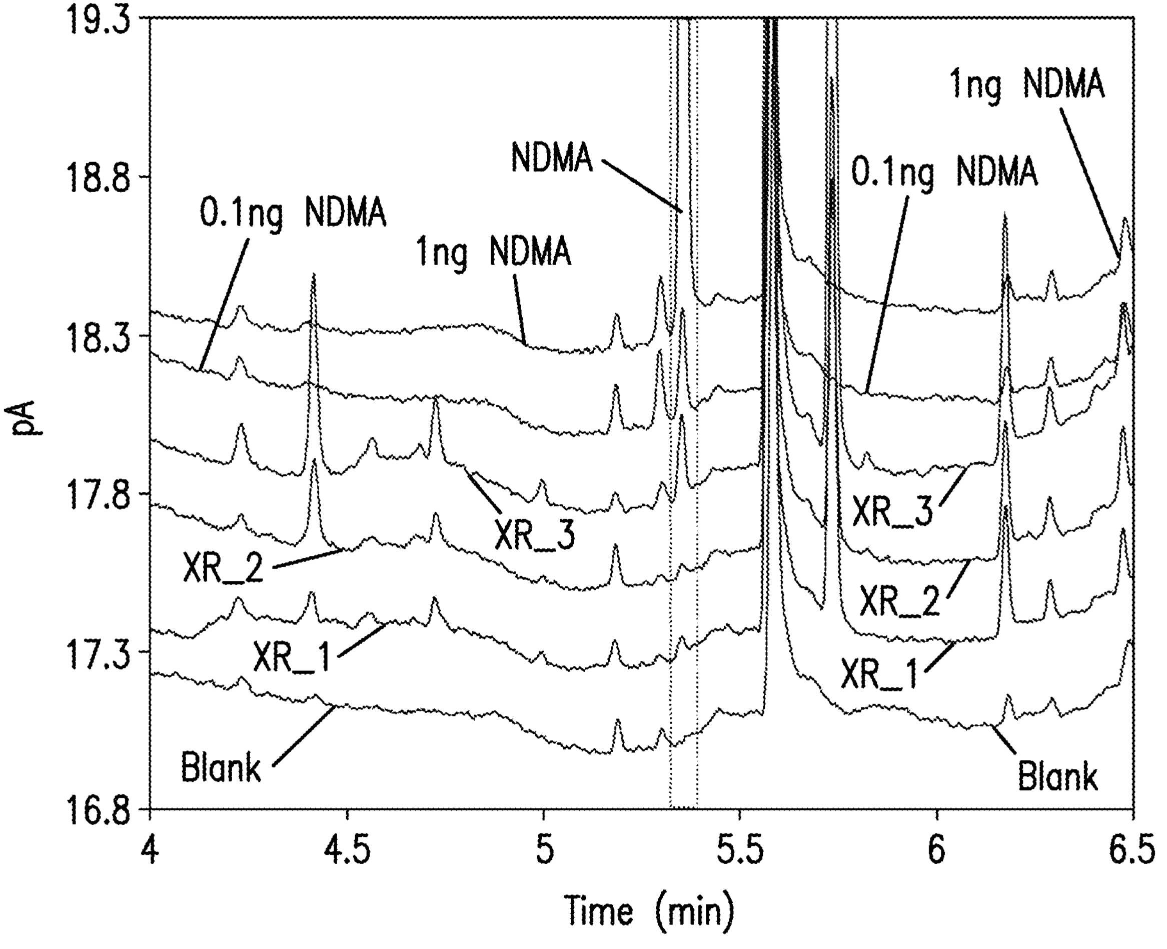
FIG. 8: Analysis of NDMA in metformin-sitagliptin extended release tablets

FIG. 8 shows the analysis of NDMA in metformin-sitagliptin extended release tablets. A DB-Wax column (30 m×0.25 mm, 0.5 μm film thickness) was used. The carrier gas was helium at a constant flow rate of 3 mL/min. The oven temperature was held at 60° C. for 1.5 min, then increased by 20° C./min to 150° C., followed by 40° C./min to 240° C., and finally held at 240° C. for 3 min. Ground tablet powder equivalent to ~21 mg metformin HCl drug substance was added to a 10 mL headspace vial, along with 50 μL diluent containing 20 mg/mL pyrogallol and 0.1% phosphoric acid in IPA. The vial was heated at 115° C. for 15 min, and 1 mL headspace was injected with a split ratio of 5:1. The quantitation limit for NDMA is 4.8 ppb, corresponding to 10% of the acceptable intake limit of 96 ng/day and maximum daily dose of 2 g.

Example 9: Analysis of NDMA in Metformin-Ertugliflozen Release Tablets

Figure 9:
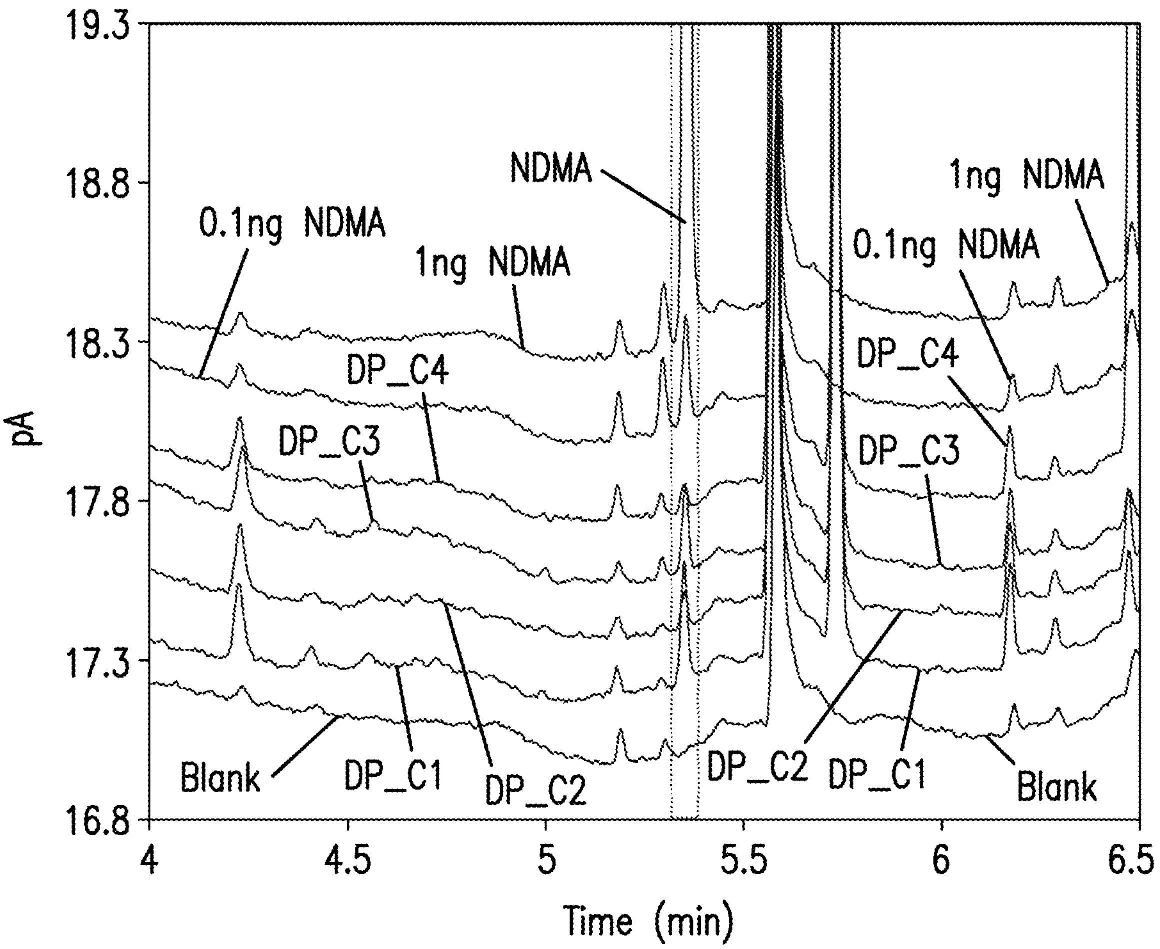
FIG. 9: Analysis of NDMA in metformin-ertugliflozen tablets

FIG. 9 shows the analysis of NDMA in metformin-ertugliflozen release tablets. A DB-Wax column (30 m×0.25 mm, 0.5 μm film thickness) was used. The carrier gas was helium at aconstant flow rate of 3 mL/min. The oven temperature was held at 60° C. for 1.5 min, then increased 20° C./min to 150° C., followed by 40° C./min to 240° C., and finally held at 240° C. for 3 min. Ground tablet powder equivalent to ~21 mg metformin HCl drug substance was added to a 10 mL headspace vial, along with 50 μL diluent containing 20 mg/mL pyrogallol and 0.1% phosphoric acid in IPA. The vial was heated at 115° C. for 15 min, and 1 mL headspace was injected with a split ratio of 5:1. The quantitation limit for NDMA is 4.8 ppb, corresponding to 10% of the acceptable intake limit of 96 ng/day and maximum daily dose of 2 g.

Example 10: Analysis of NDMA in Valsartan Drug Substance

Figure 10:
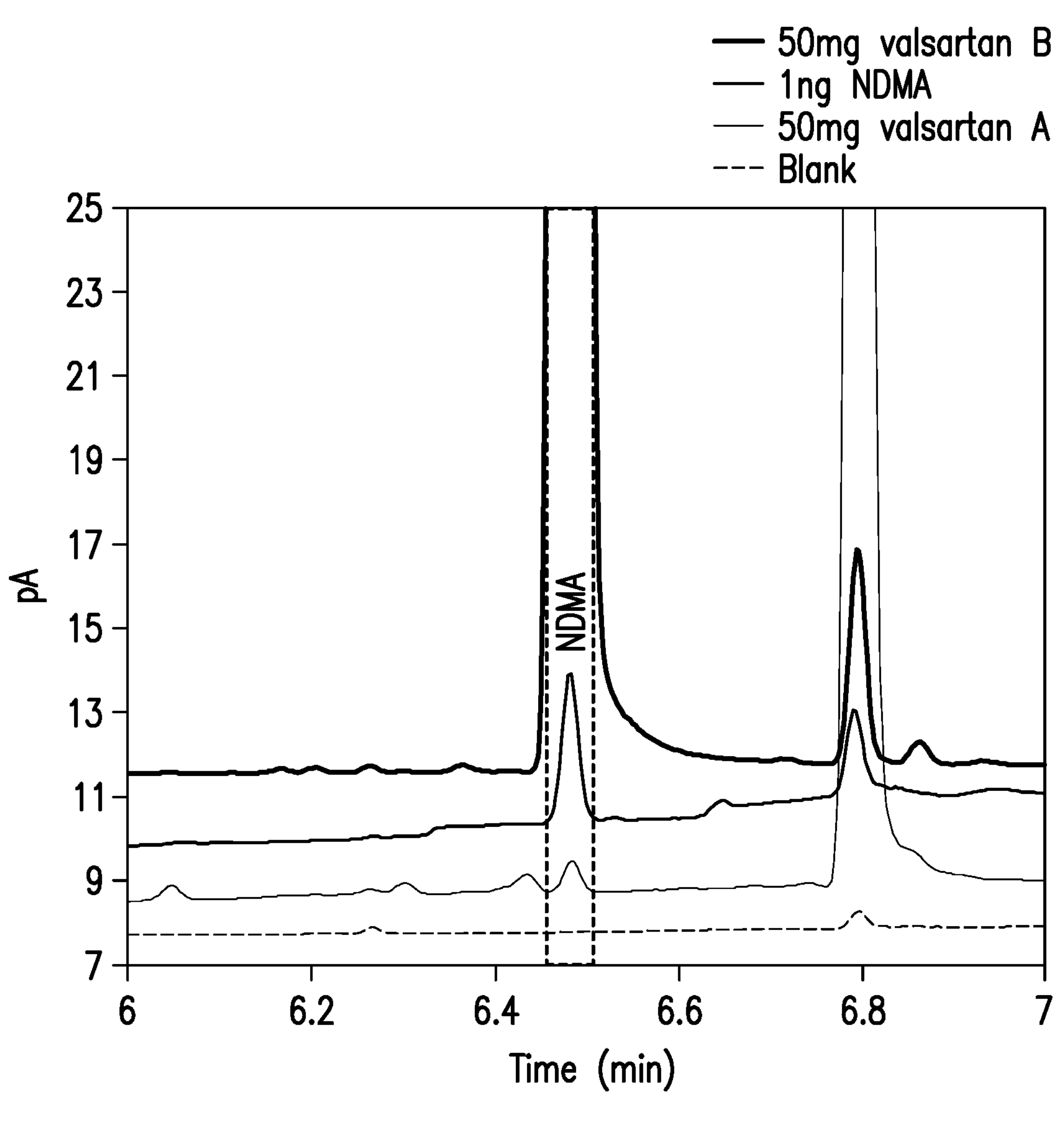
FIG. 10: Analysis of NDMA in valsartan drug substance

FIG. 10 shows the analysis of NDMA in valsartan drug substance. A DB-Wax column (30 m×0.25 mm, 0.5 μm film thickness) was used. The carrier gas was helium at a constant flow rate at 3 mL/min. The oven temperature was held at 60° C. for 1.5 min, then increased by 20° C./min to 150° C., followed by 40° C./min to 240° C., and finally held at 240° C. for 3 min. Approximately 50 mg valsartan drug substance was added to a 10 mL headspace vial, along with 50 μL diluent containing 20 mg/mL pyrogallol and 0.1% phosphoric acid in IPA. The vial was heated at 115° C. for 15 min, and 1 mL headspace was injected with a split ratio of 5:1. The quantitation limit for NDMA is 2 ppb with respect to valsartan, which is below 10% of acceptable intake limit of 30 ppb.

Example 11: Analysis of NDMA in Ranitidine Hydrochloride Drug Substance

Figure 11:
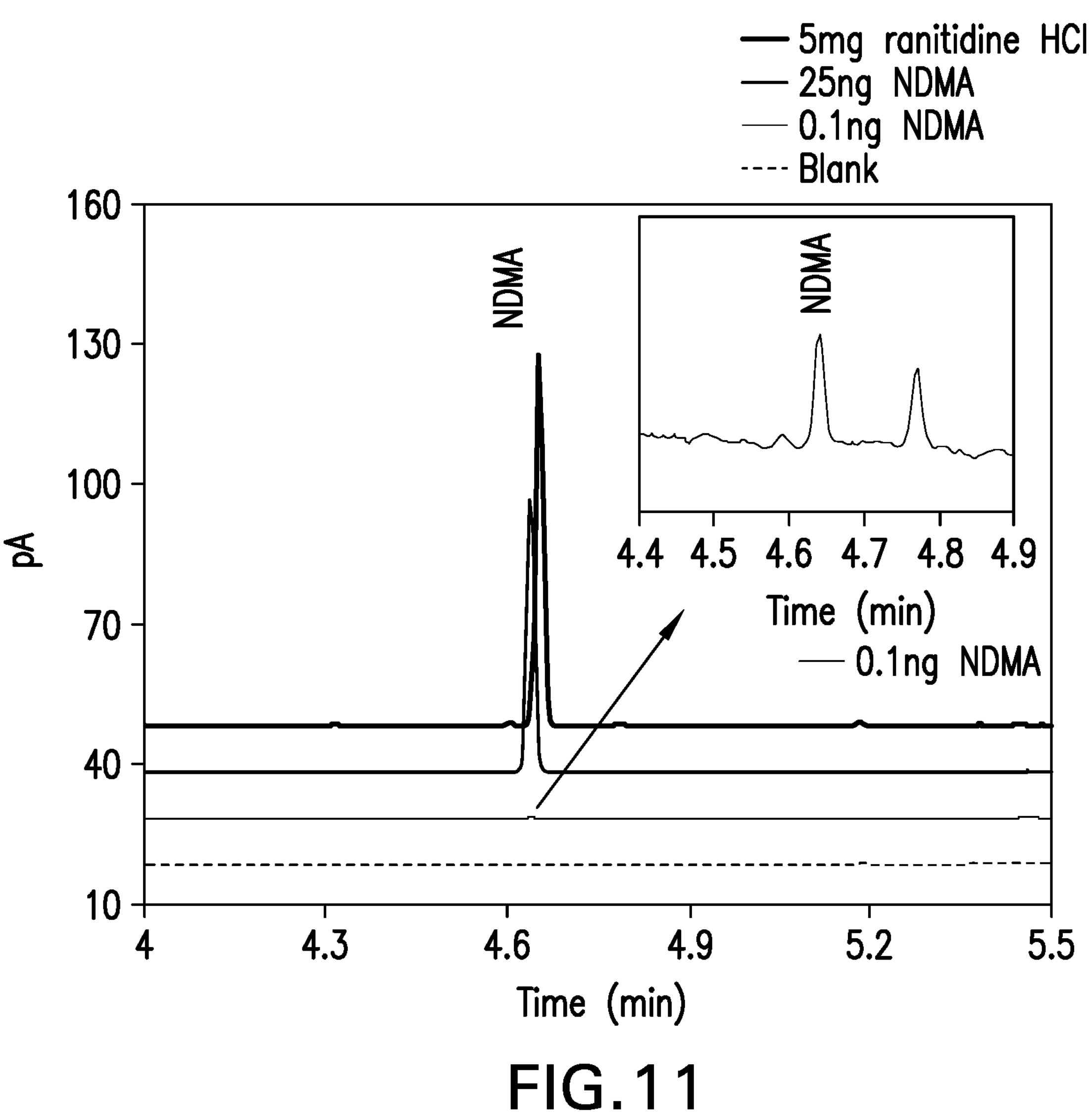
FIG. 11: Analysis of NDMA in ranitidine HCl drug substance

FIG. 11 shows the analysis of NDMA in ranitidine hydrochloride drug substance. A DB-Wax column (30 m×0.25 mm, 0.5 μm film thickness) is used. The carrier gas is helium at constant flow rate at 3 mL/min. The oven temperature is held at 60° C. for 1.5 min, then ramped by 30° C./min to 240° C., and finally held at 240° C. for 2 min. For sample preparation, 50 mg/mL ranitidine HCl was dissolved in a diluent containing 100 mg/mL pyrogallol. 20 mg/mL diphenylamine and 0.1% phosphoric acid in methanol. For GC analysis, 40 μL sample solution was transferred into a 20-mL head-space vial. The vial is equilibrated at 100° C. for 20 min, and 1 mL headspace is injected with a split ratio of 5:1. The quantitation limit for NDMA is 32 ppb with respect to ranitidine HCl, which is 10% of the acceptable intake limit of 96 ng/day and maximum daily dose of 300 mg.

Example 12: Analysis of NDMA in Ranitidine Hydrochloride Drug Substance

Figure 12:
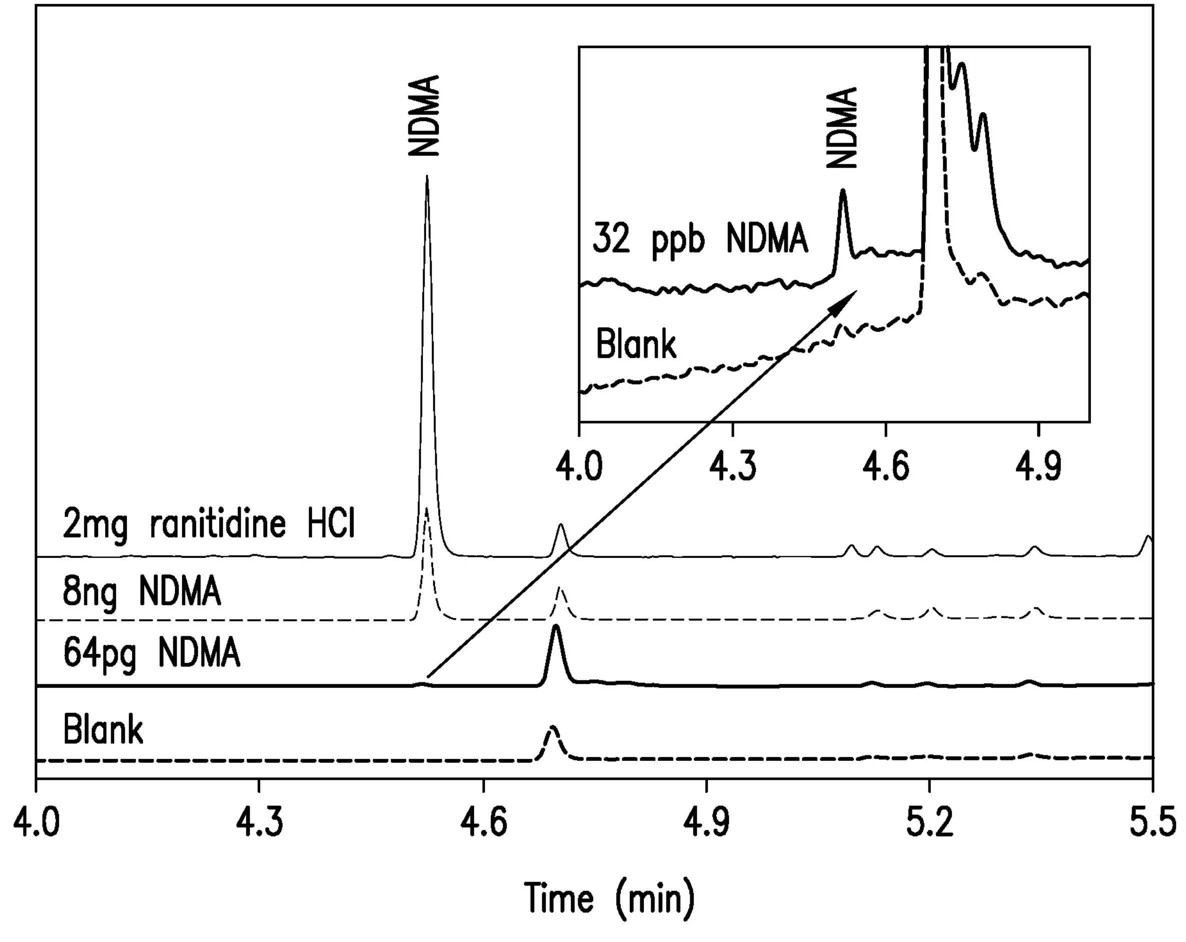
FIG. 12: Analysis of NDMA in ranitidine HCl drug substance

FIG. 12 shows an analysis of NDMA in ranitidine hydrochloride drug substance. A DB-Wax column (30 m×0.25 mm, 0.5 μm film thickness) is used. The carrier gas is helium at constant flow rate at 3 mL/min. The oven temperature is held at 60° C. for 1.5 min, then ramped by 30° C./min to 240° C., and finally held at 240° C. for 2 min. For sample preparation, 50 mg/mL ranitidine HCl was dissolved in a diluent containing 100 mg/mL pyrogallol, 20 mg/mL diphenylamine and 0.1% phosphoric acid in methanol. For GC analysis, 40 μL sample solution was transferred into a 20-mL head-space vial. The vial is equilibrated at 100° C. for 20 min, and 1 mL headspace is injected with a split ratio of 5:1. The quantitation limit for NDMA is 32 ppb with respect to ranitidine HCl, which is 10% of the acceptable intake limit of 96 ng/day and maximum daily dose of 300 mg.

Example 13: Fate and Purge Study of NDMA and NDEA in Compound A

Figure 13:
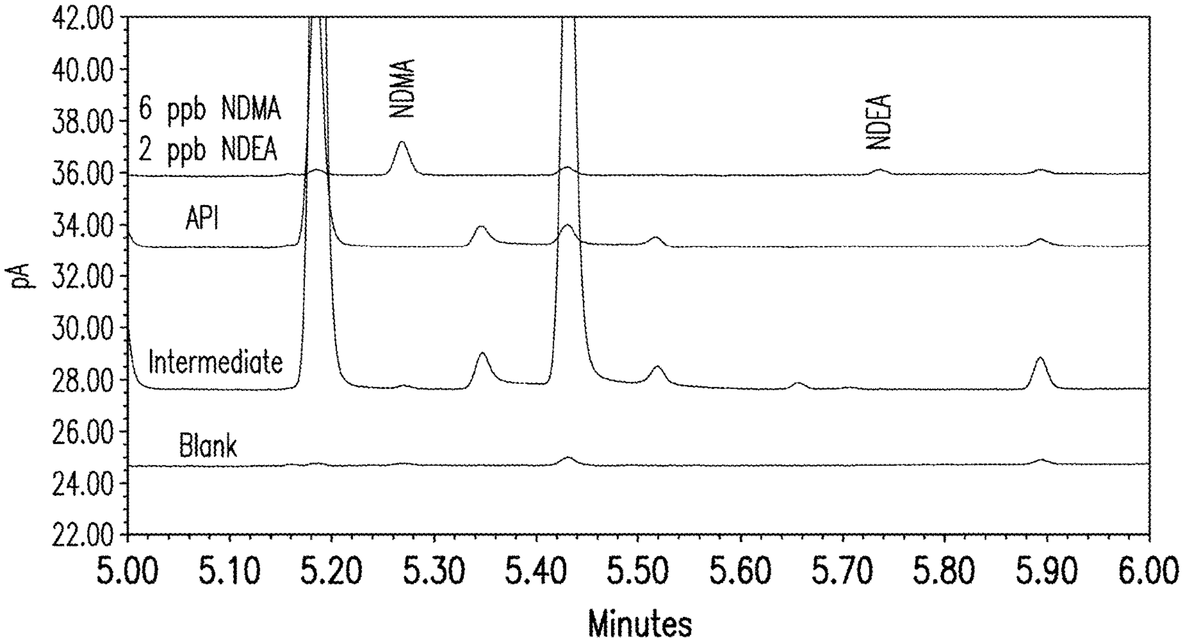
FIG. 13: Analysis of Fate and purge study of NDMA and NDEA in Compound A

FIG. 13 shows the overlaid chromatograms for the analysis of NDMA and NDEA in Compound A and its intermediate to understand the fate and purge of NDMA and NDEA in the synthesis process. A DB-Wax column (30 m×0.25 mm, 0.5 μm film thickness) is used. The carrier gas is helium at constant flow rate at 2 mL/min. The oven temperature is held at 55° C. for 1 min, then ramped by 25° C./min to 240° C., and finally held at 240° C. for 4 min. For sample preparation, 50 mg/mL Compound A or its intermediate was dissolved in a diluent containing 20 mg/mL pyrogallol in methanol. For GC analysis, 50 μL sample solution was transferred into a 20-mL head-space vial. The vial is equilibrated at 125° C. for 15 min, and 1 mL headspace is injected with a split ratio of 5:1. The quantitation limit is 6 ppb for NDMA and 2 ppb for NDEA with respect to 50 mg Compound A or its intermediate, which is 10% of the acceptable intake limit of 96 ng/day NDMA and 26.5 ng/day NDEA and maximum daily dose of 1600 mg.

Example 14: Testing for NDMA and NDEA in Compound A Drug Product

Figure 14:
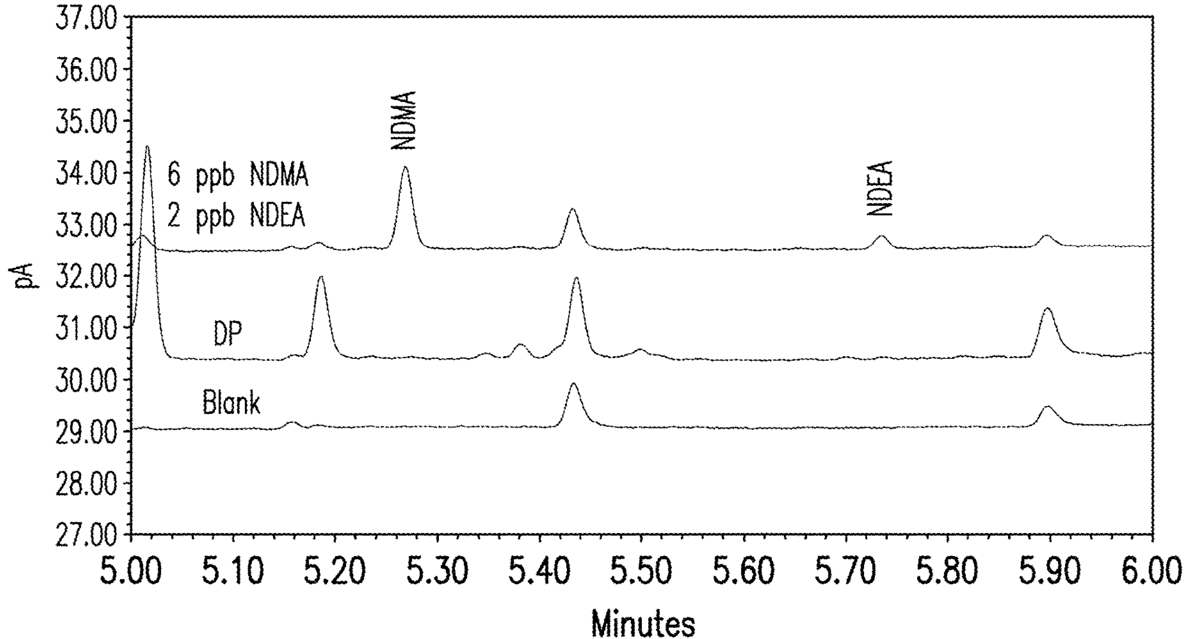
FIG. 14: Shows the overlaid chromatograms for the analysis of NDMA and NDEA in Compound A

FIG. 14 shows the overlaid chromatograms for the analysis of NDMA and NDEA in drug product with Compound A. A DB-Wax column (30 m×0.25 mm, 0.5 μm film thickness) is used. The carrier gas is helium at constant flow rate at 2 mL/min. The oven temperature is held at 55° C. for 1 min, then ramped by 25° C./min to 240° C., and finally held at 240° C. for 4 min. For sample preparation, 50 mg/mL Compound A or its intermediate was dissolved in a diluent containing 20 mg/mL pyrogallol in methanol. For GC analysis, 50 μL sample solution was transferred into a 20-mL head-space vial. The vial is equilibrated at 125° C. for 15 min, and 1 mL headspace is injected with a split ratio of 5:1. The quantitation limit is 6 ppb for NDMA and 2 ppb for NDEA with respect to 50 mg Compound A or its intermediate, which is 10% of the acceptable intake limit of 96 ng/day NDMA and 26.5 ng/day NDEA and maximum daily dose of 1600 mg.

What is claimed is:

1. A method for analyzing nitrosamines in a pharmaceutical sample wherein in situ nitrosamine formation is reduced or eliminated comprising:

a) heating a pharmaceutical sample suspected of containing one or more nitrosamines in the presence of one or more nitrosating inhibitors, b) displacing the nitrosamines from the pharmaceutical sample into a gaseous phase; and c) analyzing the nitrosamines in the gaseous phase;

wherein the nitrosating inhibitor is selected from pyrogallol, phloroglucinol, pyrrole, 2,5-dimethylpyrrole, catechol, ascorbic acid, hydrazine, propylgallate, and gallic acid in combination with diphenylamine, or N-methyl aniline.

2. The method according to claim 1 wherein the nitrosating inhibitor is pyrogallol in combination with diphenylamine.

3. The method according to claim 1 wherein the nitrosating inhibitor is in a diluent comprising an acid and solvent wherein the acid is non-volatile and selected from the group consisting of phosphoric acid, sulfuric acid, methanesulfonic acid.

4. The method according to claim 3 wherein the solvent is selected from the group consisting of methanol, acetonitrile, acetone, ethanol, isopropanol, and 1-propanol or a mixture thereof.

5. The method according to claim 3 wherein the ratio of diluent to the nitrosamine containing pharmaceutical sample is from 1:5 to 10:1.

6. The method according to claim 1 wherein the temperature of the pharmaceutical sample is heated to about 60° C. to about 200° C.

7. The method according to claim 1 wherein the nitrosamines being analyzed are semi-volatile.

8. The method according to claim 1 wherein the nitrosamines in the gaseous phase are separated and analyzed using gas chromatography (GC) coupled with a GC detector selected from the group consisting of mass spectrometer (MS), nitrogen-phosphorus detector (NPD), thermal energy analyzer (TEA), nitrogen chemiluminescence detector (NCD) or flame ionization detector (FID).

9. The method according to claim 1 wherein the method for analyzing nitrosamines is selected from liquid injection GC-NPD, headspace GC-NPD or full evaporation headspace GC with NPD (FE-HSGC-NPD).

10. The method according to claim 1 wherein the method for analyzing nitrosamines is full evaporation headspace GC with NPD.

11. A method for analyzing nitrosamine analytes in pharmaceutical samples wherein in situ nitrosamine formation is reduced or eliminated, comprising:

a) heating a pharmaceutical sample suspected of containing one or more nitrosamine analytes in the presence of one or more nitrosating inhibitors selected from the group consisting of pyrogallol, phloroglucinol, pyrrole, 2,5-dimethylpyrrole, catechol, ascorbic acid, hydrazine, propylgallate, and/or gallic acid in combination with diphenylamine, or N-methyl aniline;

b) displacing the nitrosamine(s) analytes into a gaseous phase; and c) analyzing the nitrosamine analytes.

12. The method according to claim 11 wherein the nitrosating inhibitor is in a diluent comprising an acid and solvent wherein the acid is non-volatile and selected from the group consisting of phosphoric acid, sulfuric acid, methanesulfonic acid and the solvent is selected from the group consisting of methanol, acetonitrile, acetone, ethanol, isopropanol, and 1-propanol or a mixture thereof.

13. The method according to claim 11 wherein the temperature of the pharmaceutical sample is heated to about 60° C. to about 200° C.

14. The method according to claim 11 wherein the nitrosamine analytes being analyzed are semi-volatile.

15. The method according to claim 11 wherein the nitrosamine(s) in the gaseous phase are separated and analyzed using gas chromatography (GC) coupled with a GC detector selected from the group consisting of mass spectrometer (MS), nitrogen-phosphorus detector (NPD), thermal energy analyzer (TEA), nitrogen chemiluminescence detector (NCD) or flame ionization detector (FID).

16. The method according to claim 11 wherein the method for analyzing nitrosamines is selected from liquid injection GC-NPD, headspace GC-NPD or full evaporation headspace GC with NPD (FE-HSGC-NPD).

17. The method according to claim 11 wherein the method for analyzing nitrosamines is full evaporation headspace GC with NPD (FE-HSGC-NPD).

* * * * *